US012751609B2

(12) United States Patent
Iwasaki

(10) Patent No.: US 12,751,609 B2
(45) Date of Patent: Oct. 6, 2026

(54) FLUID FEEDING AND SUCTION APPARATUS, ENDOSCOPE SYSTEM, AND METHOD OF SUCTION RESIDUE BY ENDOSCOPE SYSTEM

(71) Applicant: OLYMPUS MEDICAL SYSTEMS CORP., Tokyo (JP)

(72) Inventor: Seiji Iwasaki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 546 days.

(21) Appl. No.: 18/102,906

(22) Filed: Jan. 30, 2023

(65) Prior Publication Data

US 2023/0255448 A1 Aug. 17, 2023

Related U.S. Application Data

(60) Provisional application No. 63/309,120, filed on Feb. 11, 2022.

(51) Int. Cl.
*A61B 1/12* (2006.01)
*A61B 1/00* (2006.01)
(Continued)

(52) U.S. Cl.
CPC ............ *A61B 1/12* (2013.01); *A61B 1/00068* (2013.01); *A61B 1/015* (2013.01); *A61M 1/77* (2021.05); *A61M 1/772* (2021.05); *A61B 1/126* (2013.01)

(58) Field of Classification Search
CPC ............ A61B 1/00094; A61B 1/00112; A61B 1/00119; A61B 1/015; A61B 1/0661; A61B 1/126; A61B 1/127; A61B 1/128
See application file for complete search history.

(56) References Cited

U.S. PATENT DOCUMENTS 4,552,130 A 11/1985 Kinoshita
5,191,878 A * 3/1993 Iida ........................ A61B 1/126 600/157
(Continued)

FOREIGN PATENT DOCUMENTS

CN 1550203 A 12/2004
CN 104812287 A 7/2015
(Continued)

OTHER PUBLICATIONS

Office Action dated Jul. 18, 2025, issued in corresponding Chinese Patent Application No. 202211433361.6.

*Primary Examiner* — Ryan N Henderson
(74) *Attorney, Agent, or Firm* — Morgan, Lewis & Bockius LLP

(57) ABSTRACT

A fluid feeding and suction apparatus includes a common conduit including an endoscopic connection end and a second end, a fluid feeding conduit in fluid communication with the common conduit via the branching connector, a fluid suction conduit in fluid communication with the common conduit via the branching connector, a fluid feeding container connected to the fluid feeding conduit, a fluid suction container connected to the fluid suction conduit, a gas feeding conduit connected to the fluid feeding container, a gas suction conduit connected to the fluid suction container, and a pump connected to the gas feeding conduit and the gas suction conduit. The second end connected to a branching connector. The pump is configured to feed a supply gas to the gas feeding conduit and to suction a suction gas from the gas suction conduit.

20 Claims, 6 Drawing Sheets

(51) Int. Cl.

*A61B 1/015* (2006.01)
*A61M 1/00* (2006.01)

(56) References Cited

U.S. PATENT DOCUMENTS

| | | | | |
|---|---|---|---|---|
| 5,609,563 | A * | 3/1997 | Suzuki | A61B 1/00098 600/118 |
| 5,630,795 | A * | 5/1997 | Kuramoto | A61B 1/00137 604/35 |
| 5,879,288 | A * | 3/1999 | Suzuki | A61B 1/00124 600/176 |
| 9,345,386 | B1 * | 5/2016 | Cheng | A61B 1/00135 |
| 2005/0119527 | A1 * | 6/2005 | Banik | A61B 1/00066 600/117 |
| 2006/0052665 | A1 * | 3/2006 | Aizenfeld | A61M 1/77 600/158 |
| 2006/0106285 | A1 * | 5/2006 | Boulais | A61B 1/128 600/156 |
| 2006/0116552 | A1 * | 6/2006 | Noguchi | A61B 1/121 600/132 |
| 2006/0266423 | A1 | 11/2006 | Akiba et al. | |
| 2007/0027359 | A1 * | 2/2007 | Salman | A61B 1/015 600/158 |
| 2007/0043262 | A1 * | 2/2007 | Levy | A61B 1/015 600/156 |
| 2007/0060789 | A1 * | 3/2007 | Uchimura | A61B 1/00105 600/110 |
| 2007/0238929 | A1 * | 10/2007 | Aizenfeld | A61B 1/015 600/158 |
| 2007/0276352 | A1 * | 11/2007 | Crocker | A61B 10/025 604/35 |
| 2008/0154185 | A1 * | 6/2008 | Blight | A61B 1/015 604/35 |
| 2009/0131827 | A1 * | 5/2009 | Crocker | A61B 10/025 604/22 |
| 2010/0185056 | A1 * | 7/2010 | Gordon | A61M 25/0105 600/158 |
| 2013/0310647 | A1 * | 11/2013 | Milton | A61B 1/00135 600/155 |
| 2015/0087907 | A1 | 3/2015 | Konstorum et al. | |
| 2015/0087911 | A1 * | 3/2015 | Konstorum | A61B 1/00091 600/157 |
| 2015/0196735 | A1 | 7/2015 | Olig et al. | |
| 2015/0250958 | A1 | 9/2015 | Hayashi et al. | |
| 2016/0206805 | A1 * | 7/2016 | Hassidov | A61M 1/77 |
| 2017/0224197 | A1 * | 8/2017 | Green | A61B 1/126 |
| 2020/0163540 | A1 | 5/2020 | Sato | |
| 2020/0187768 | A1 * | 6/2020 | Shelton | A61B 18/26 |
| 2022/0192479 | A1 * | 6/2022 | Harris | B08B 5/02 |

FOREIGN PATENT DOCUMENTS

| | | | |
|---|---|---|---|
| CN | 105491938 | A | 4/2016 |
| CN | 107374577 | A | 11/2017 |
| JP | S59-160431 | A | 9/1984 |
| JP | H04-325140 | A | 11/1992 |
| JP | 2001-061775 | A | 3/2001 |
| JP | 2005-131163 | A | 5/2005 |
| JP | 2006-325814 | A | 12/2006 |
| JP | 2012-075746 | A | 4/2012 |
| JP | 2016-140574 | A | 8/2016 |
| JP | 2017-504411 | A | 2/2017 |
| WO | 2019/044041 | A1 | 3/2019 |

* cited by examiner

FLUID FEEDING AND SUCTION APPARATUS, ENDOSCOPE SYSTEM, AND METHOD OF SUCTION RESIDUE BY ENDOSCOPE SYSTEM

RELATED APPLICATION DATA

This application is based on and claims priority under 35 U.S.C. § 119 to U.S. Provisional Application No. 63/309,120 filed on Feb. 11, 2022, the entire contents of which are incorporated herein by reference.

FIELD OF DISCLOSURE

The present disclosure relates to a fluid feeding and suction apparatus configured to suction and remove foreign matter in a subject, an endoscope system and a method of suction residue by the endoscope system.

BACKGROUND

Conventionally, when performing endoscopic observation, treatment and the like with a medical endoscope under an emergency situation in which an inside of a body such as a stomach is bleeding, for example, an operator identify a site of bleeding while suction and removing foreign matter such as undigested food and blood in the stomach.

As described in Japanese Patent Application Laid-Open Publication No. 2001-61775, for example, there is known a procedure of injecting liquid like clean water from a syringe through a treatment instrument insertion channel of an endoscope, for the purposes of cleaning bleeding sites in a body, removing waste and the like.

SUMMARY OF THE DISCLOSURE

A fluid feeding and suction apparatus includes a common conduit, a fluid feeding conduit, a fluid suction conduit, a fluid feeding container, a fluid suction container, a gas feeding conduit, a gas suction conduit and a pump. The common conduit includes an endoscopic connection end and a second end, the second end connected to a branching connector. The fluid feeding conduit is in fluid communication with the common conduit via the branching connector. The fluid suction conduit is in fluid communication with the common conduit via the branching connector. The fluid feeding container is connected to the fluid feeding conduit. The fluid suction container is connected to the fluid suction conduit. The gas feeding conduit is connected to the fluid feeding container. The gas suction conduit is connected to the fluid suction container. The pump is connected to the gas feeding conduit and the gas suction conduit, and is configured to feed a supply gas to the gas feeding conduit and to suction a suction gas from the gas suction conduit.

A method for suctioning with a fluid feeding and suction apparatus, comprising, connecting an endoscopic connection end of a common conduit of a fluid feeding and suction apparatus to an opening of an endoscope, and operating a pump of the fluid feeding and suction apparatus in a first mode, wherein, in the first mode, operating the pump results in a negative pressure in a fluid suction container of the fluid feeding and suction apparatus.

DETAILED DESCRIPTION

Hereinafter, a configuration of one aspect of the present disclosure is described. Note that in the following explanation, the drawings based on each embodiment are schematic, and attention should be paid to the fact that the relationship between the thickness and the width of each part, ratios of the thicknesses of respective parts and the like are different from the actual relationship and ratios. Further, there may be parts where the relationships and ratios of mutual dimensions are different among the drawings.

When insoluble matter, foreign matter or the like that is residue such as undigested food and coagulated blood in a subject (hereinafter, simply referred to as in a body), for example, in a stomach is clogged in a treatment instrument insertion channel, in an endoscope, it is possible to discharge the foreign matter clogged in the treatment instrument insertion channel from a distal end of an insertion portion by connecting a syringe to a treatment instrument insertion portion of an operation portion and feeding a liquid as in the conventional art.

However, in the conventional endoscope, in a process of suctioning foreign matter, complicated work of switching a suction operation to a liquid feeding operation is required after the syringe is fitted to the treatment instrument insertion portion. Therefore, there has been a problem that a procedure such as identification of a bleeding site by the endoscope cannot proceed quickly.

Thus, the fluid feeding and suction apparatus of an endoscope, an endoscope system, and a method of suctioning residue by an endoscope of the present embodiment can realize a configuration that can easily switch the suction operation and the liquid feeding operation, and suction foreign matter in a body so as to be able to identify a bleeding site quickly.

Figure 1:
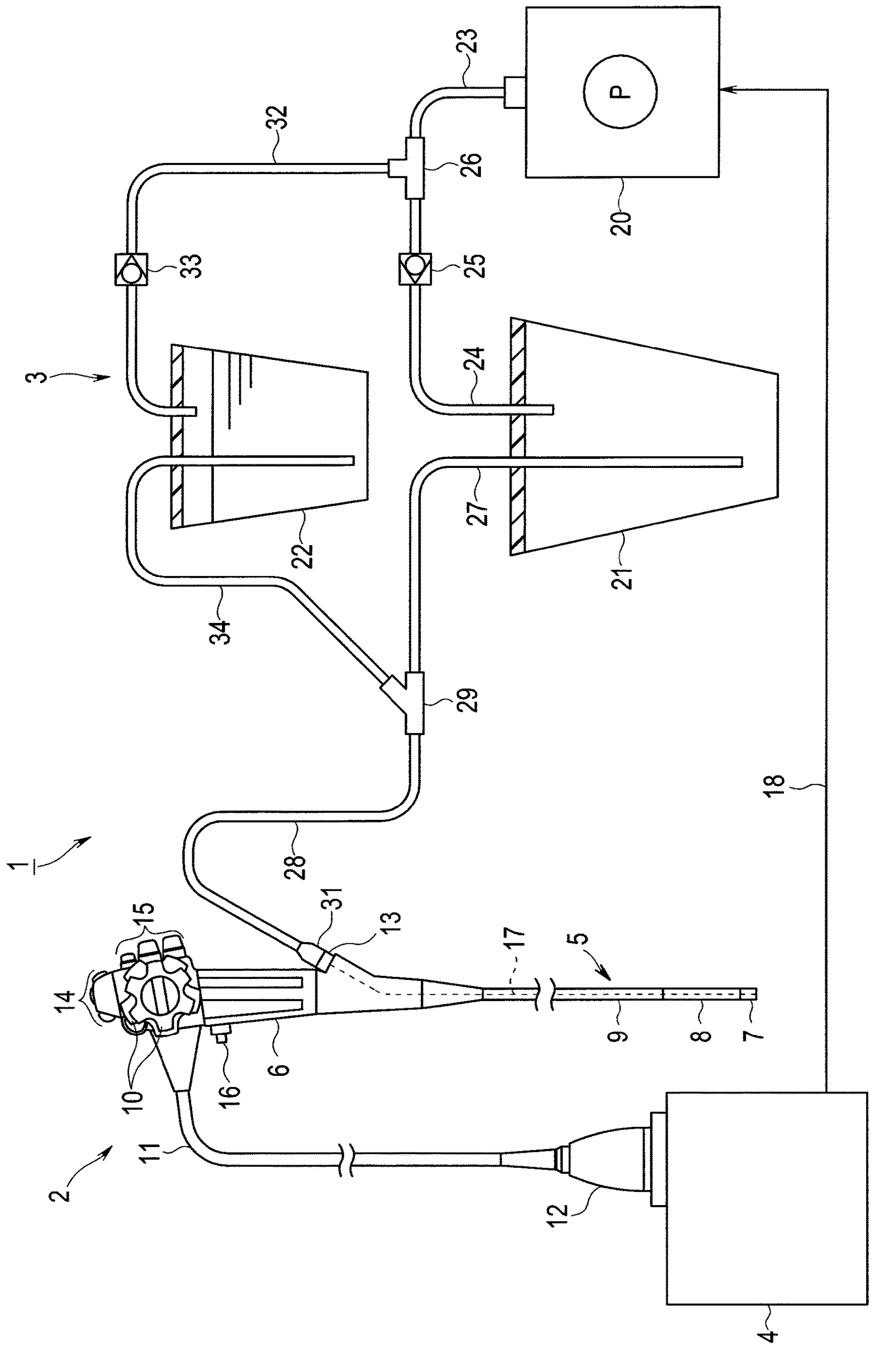
FIG. 1 is a view schematically showing an endoscope system of one aspect of the present disclosure.

Hereinafter, an endoscope system 1 of the present embodiment is described. The endoscope system 1 is configured by an endoscope 2, a fluid feeding and suction apparatus 3, and a video processor 4 of a camera control unit (CCU), as show in FIG. 1.

First, a schematic configuration of the endoscope 2 of the present embodiment is described. The endoscope 2 has an insertion portion 5, an operation portion 6, and a universal cord 11.

The insertion portion 5 is a long member insertable into an inside of a subject. The insertion portion 5 has a distal end portion 7, a bending portion 8, and a flexible tube portion 9.

The distal end portion 7 is placed at a distal end of the insertion portion 5. The bending portion 8 is placed at a proximal end side of the distal end portion 7. The bending portion 8 is bendable. The flexible tube portion 9 has flexibility, and is placed at a proximal end side of the bending portion 8. The flexible tube portion 9 is connected to a distal end side of the operation portion 6.

At the distal end portion 7, an observation window (not illustrated) is provided. Photographing light that enters from the observation window is photoelectrically changed by an image sensor (not illustrated) contained in the distal end portion 7. An image pickup cable that extends from the image sensor is placed to an endoscope connector 12 by being inserted through the insertion portion 5, the operation portion 6, and the universal cord 11.

The operation portion 6 has a treatment instrument insertion opening 13 that is a forceps introduction portion as a treatment instrument insertion opening. The treatment instrument insertion opening 13 communicates with a treatment instrument insertion channel 17 (channel) that is an endoscope conduit. The treatment instrument insertion channel 17 is placed in the operation portion 6 and the insertion portion 5. The treatment instrument insertion channel 17 opens at the distal end portion 7. The endoscope includes the treatment instrument insertion opening 13, a distal end opening, and the channel 17 connecting the treatment instrument insertion opening 13 and the distal end opening, and the endoscopic connection end 31 of the fluid feeding and suction apparatus 3 is connected to the treatment instrument insertion opening 13 of the endoscope.

At the operation portion 6, an angle knob 10 for operating bending of the bending portion 8 is provided. The operation portion 6 is provided with a plurality of switch buttons 14 configured to operate freeze of an endoscope image, release of image pickup and the like, a plurality of buttons 15 configured to operate endoscope functions, a control button 16 (control switch) that is a control switch configured to operate a gas feeding and suction pump unit 20 (pump) of the fluid feeding and suction apparatus 3, and the like. The operation portion includes a controller configured to switch rotation direction of the pump 20, and the control switch 16 configured to transmit a signal to the controller. The controller and the control switch 16 may be provided on the video processor 4 or the pump 20.

Note that the control button 16 may be configured to be removable from the operation portion 6. Further, the control button 16 may be a foot switch.

The universal cord 11 is a composite cable extending from a side portion of the operation portion 6. In the universal cord 11, the endoscope connector 12 is provided at an extension end. The endoscope connector 12 is connected to the video processor 4 of the camera control unit (CCU) including a light source apparatus.

The video processor 4 is electrically connected to the gas feeding and suction pump unit 20 of the fluid feeding and suction apparatus 3 by a control cable 18. The video processor 4 contains a light source that emits illumination light that is transmitted to a light guide bundle not illustrated and inserted through the universal cord 11, the operation portion 6, and the insertion portion 5.

The illumination light generated from the video processor 4 is emitted from an illumination window (not illustrated) provided at the distal end portion 7 of the insertion portion 5. Note that in the endoscope 2, the light source such as an LED may be contained in the distal end portion 7 as an illumination apparatus.

The endoscope 2 configured as above may be a disposable (single-use) single-use endoscope that is discarded after use, but may be a reuse product that is reused after being subjected to disinfection sterilization treatment as a matter of course.

Next, a schematic configuration of the fluid feeding and suction apparatus 3 of the present embodiment is described. The fluid feeding and suction apparatus 3 has the gas feeding and suction pump unit 20, a liquid draining tank 21 (fluid suction container) that is a suction tank, and a liquid feeding tank 22 in which a biocompatible fluid such as physiological saline is stored.

In the gas feeding and suction pump unit 20, one end is connected to a pump tube 23 as a conduit. In the pump tube 23, the other end is connected to a T-tube 26 of a T-shaped conduit.

To the T-tube 26, one end of each of a gas suction tube 24 (gas suction conduit) and a gas feeding tube 32 (gas feeding conduit) that are conduits are connected. In the gas suction tube 24, the other end is connected to the liquid draining tank 21. In the gas suction tube 24, the other end is disposed on a surface portion side of the liquid draining tank 21.

A check valve 25 is interposed in a middle of the gas suction tube 24. The check valve 25 is configured such that an internal valve is closed by gas feeding back pressure to a liquid draining tank 21 side by the gas feeding and suction pump unit 20. Therefore, in the gas suction tube 24, gas (air) does not flow to the liquid draining tank 21 side from the check valve 25. The check valve 25 is provided in the gas suction conduit 24, the check valve 25 configured to allow the suction gas to flow from the fluid suction container 21 to the pump 20, and is configured to prevent the suction gas from flowing from the pump 20 to the fluid suction container 21. The fluid feeding container 22 includes a first interior space, and a first end of the gas feeding conduit 32 is located in the first interior space. The fluid suction container 21 includes a second interior space, and a first end of the gas suction conduit 24 is located in the second interior space.

On the other hand, in the check valve 25, the internal valve opens by the gas feeding and suction pump unit 20 suctioning gas. Therefore, gas (air) flows to the gas feeding and suction pump unit 20 side from the check valve 25.

A liquid draining tube 27 (fluid suction conduit) that is a conduit is connected to the liquid draining tank 21. The liquid draining tube 27 is disposed so that one end extends to a vicinity of a bottom portion of the liquid draining tank 21. Note that in the liquid draining tube 27, the other end is connected to a Y-tube 29 of a Y-shaped conduit.

One end of a fluid feeding and suction tube 28 that is a conduit is connected to the Y-tube 29 (branching connector). A treatment instrument insertion opening connector 31 (endoscopic connection end) is provided at the other end of the fluid feeding and suction tube 28 (common conduit). The fluid feeding and suction apparatus 3 includes the common conduit 28 including the endoscopic connection end 31 and a second end 29, the second end connected to a branching connector 29.

The treatment instrument insertion opening connector 31 is connected to the treatment instrument insertion opening 13 of the operation portion 6 with airtightness (watertightness). The treatment instrument insertion opening connector 31 is removable from the treatment instrument insertion opening 13.

In the gas feeding tube 32 that is a conduit, the other end is connected to the liquid feeding tank 22. In the gas feeding tube 32, the other end is disposed in a vicinity of a surface portion of the liquid feeding tank 22.

A check valve 33 is interposed in a middle of the gas feeding tube 32. In the check valve 33, an internal valve is closed by a suction gas back pressure to a T-tube 26 side by the gas feeding and suction pump unit 20. Thereby, in the gas feeding tube 32, gas (air) does not flow to a T-tube 26 side and a gas feeding and suction pump unit 20 side from the check valve 33. The check valve 33 is provided in the gas feeding conduit 32, the check valve 33 is configured to allow the supply gas to flow from the pump 20 to the fluid feeding container 22 and is configured to prevent the supply gas from flowing from the fluid feeding container 22 to the pump 20.

On the other hand, in the check valve 33, the internal valve opens by the gas feeding and suction pump unit 20 feeding gas. Therefore, in the gas feeding tube 32, gas (air) flows to a liquid feeding tank 22 (fluid feeding container) side from the check valve 33.

A liquid feeding tube 34 (fluid feeding conduit) that is a conduit is connected to the liquid feeding tank 22. In the liquid feeding tube 34, one end is disposed to extend to a vicinity of a bottom portion of the liquid feeding tank 22. Note that in the liquid feeding tube 34, the other end is connected to the Y-tube 29. The fluid feeding conduit 34 is in fluid communication with the common conduit 28 via the branching connector 29. The fluid suction conduit 27 is in fluid communication with the common conduit 28 via the branching connector 29. The fluid feeding container 22 is connected to the fluid feeding conduit. The fluid suction container 21 is connected to the fluid suction conduit 27. The gas feeding conduit 32 is connected to the fluid feeding container 22. The gas suction conduit 24 is connected to the fluid suction container 21. The pump 20 is connected to the gas feeding conduit 32 and the gas suction conduit 24, and is configured to feed a supply gas to the gas feeding conduit 32 and to suction a suction gas from the gas suction conduit 24.

In this way, the fluid feeding and suction apparatus 3 is in a conduit form that is branched into two by the Y-tube 29 from the fluid feeding and suction tube 28 connected to the treatment instrument insertion opening 13 of the endoscope 2.

The liquid draining tube 27 that is branched by the Y-tube 29 is connected to the liquid draining tank 21 that is at a downstream side. The gas suction tube 24 of the conduit that is at a downstream side is connected to the liquid draining tank 21. In the gas suction tube 24, the check valve 25 that prevents backflow is provided in the middle.

In this way, in the fluid feeding and suction apparatus 3, the form of a liquid draining conduit passing through the liquid draining tank 21 from the treatment instrument insertion opening 13 of the endoscope 2 is configured.

On the other hand, the liquid feeding tube 34 that is branched by the Y-tube 29 is connected to the liquid feeding tank 22 that is at an upstream side. The gas feeding tube 32 at an upstream side is connected to the liquid feeding tank 22. In the gas feeding tube 32, the check valve 33 that prevents backflow is provided in the middle.

The gas suction tube 24 and gas feeding tube 32 join each other by the T-tube 26 provided in front of the gas feeding and suction pump unit 20. The T-tube 26 is connected to the gas feeding and suction pump unit 20 by the pump tube 23.

In this way, in the fluid feeding and suction apparatus 3 of the present embodiment, a form of a liquid feeding conduit passing through the liquid feeding tank 22 from the treatment instrument insertion opening 13 of the endoscope 2 is formed.

Here, an operation of feeding a liquid into an inside of a body or suctioning foreign matter, from the treatment instrument insertion channel 17 of the endoscope 2 by drive of the fluid feeding and suction apparatus 3 in the endoscope system 1 is described.

In the endoscope system 1, a user who is a doctor can switch gas feeding, gas suctioning and stop of the gas feeding and suction pump unit 20 of the fluid feeding and suction apparatus 3 by operating the control button 16 provided at the operation portion 6.

Note that a control signal by the operation of the control button 16 is outputted from the video processor 4 to the gas feeding and suction pump unit 20 connected to the control cable 18. Subsequently, in the gas feeding and suction pump unit 20, an internal pump drives in a predetermined forward or reverse rotation direction based on the inputted control signal, and thereby switching between gas feeding and gas suction is determined.

In this way, the endoscope system 1 is configured to feed a liquid into a body or suction foreign matter in the body through (via) the treatment instrument insertion channel 17 of the endoscope 2 by a switching operation of gas feeding or gas suction by the gas feeding and suction pump unit 20 of the fluid feeding and suction apparatus 3.

Figure 2:
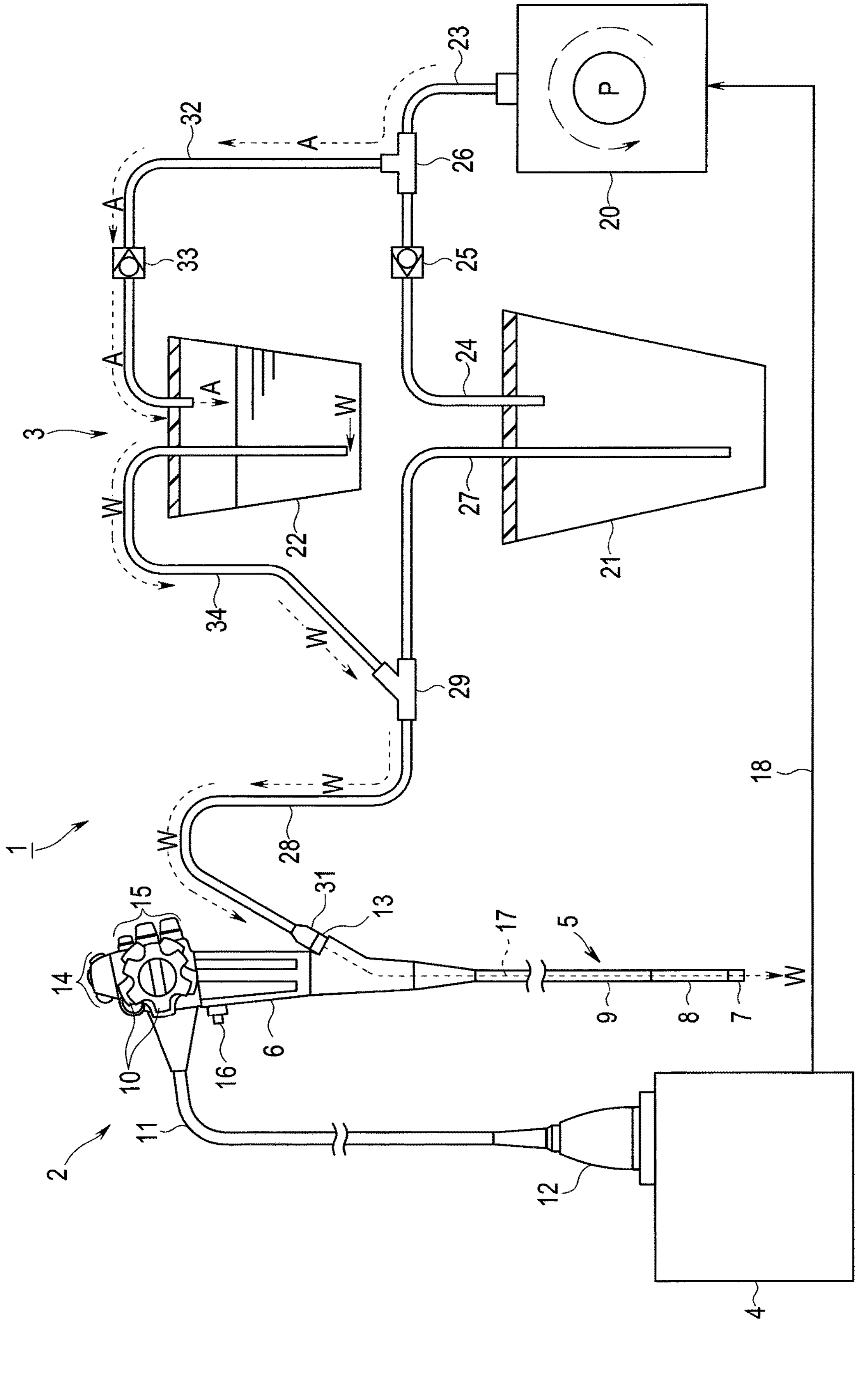
FIG. 2 is a view schematically showing the endoscope system in a liquid feeding mode.

In the endoscope system 1, the control button 16 is operated in a predetermined manner, when liquid feeding is performed, and thereby the gas feeding and suction pump unit 20 drives in a predetermined rotation direction as shown in FIG. 2. Air A that is fed from the gas feeding and suction pump unit 20 is fed into the liquid feeding tank 22 through the pump tube 23, the T-tube 26, and the gas feeding tube 32.

At this time, the valve in the check valve 33 provided in the gas feeding tube 32 opens by the air A that is fed, and the air A is fed into the liquid feeding tank 22. Note that in the check valve 25 provided in the gas suction tube 24, the internal valve is closed by feeding back pressure of the air A. Therefore, the air A is blocked by the check valve 25, and is not fed into the liquid draining tank 21.

In the liquid feeding tank 22, a liquid W such as physiological saline stored inside is fed by pressure by the air A, and thereby flows into the liquid feeding tube 34. The liquid W flows into the treatment instrument insertion channel 17 of the endoscope 2 through the Y-tube 29, and the fluid feeding and suction tube 28. The fluid feeding container 22 is configured to contain physiological saline, and the fluid suction container 21 is configured to contain fluid such as undigested food, coagulated blood in a subject and the physiological saline fed.

In this way, the liquid W that is fed into the treatment instrument insertion channel 17 is fed into the body from the distal end portion 7 of the insertion portion 5. Note that during the liquid feeding, the liquid draining tank 21 is hermetically closed, so that the liquid W flowing in the liquid feeding tube 34 does not flow into the liquid draining tube 27 from the Y-tube 29.

In this way, in the endoscope system 1, a liquid feeding mode for feeding the liquid W that is a biocompatible fluid such as physiological saline into the body from the distal end portion 7 of the insertion portion 5 by bringing the gas feeding conduit system under positive pressure is executed.

Therefore, the endoscope system 1 is operated in the liquid feeding mode when foreign matter S including insoluble matter that is residue such as undigested food and coagulated blood in a body, for example, in a stomach is clogged in the treatment instrument insertion channel 17. Thereby, it is possible to temporarily discharge the foreign matter S that is the residue clogged in the treatment instrument insertion channel 17 into the body from the distal end portion 7.

Figure 3:
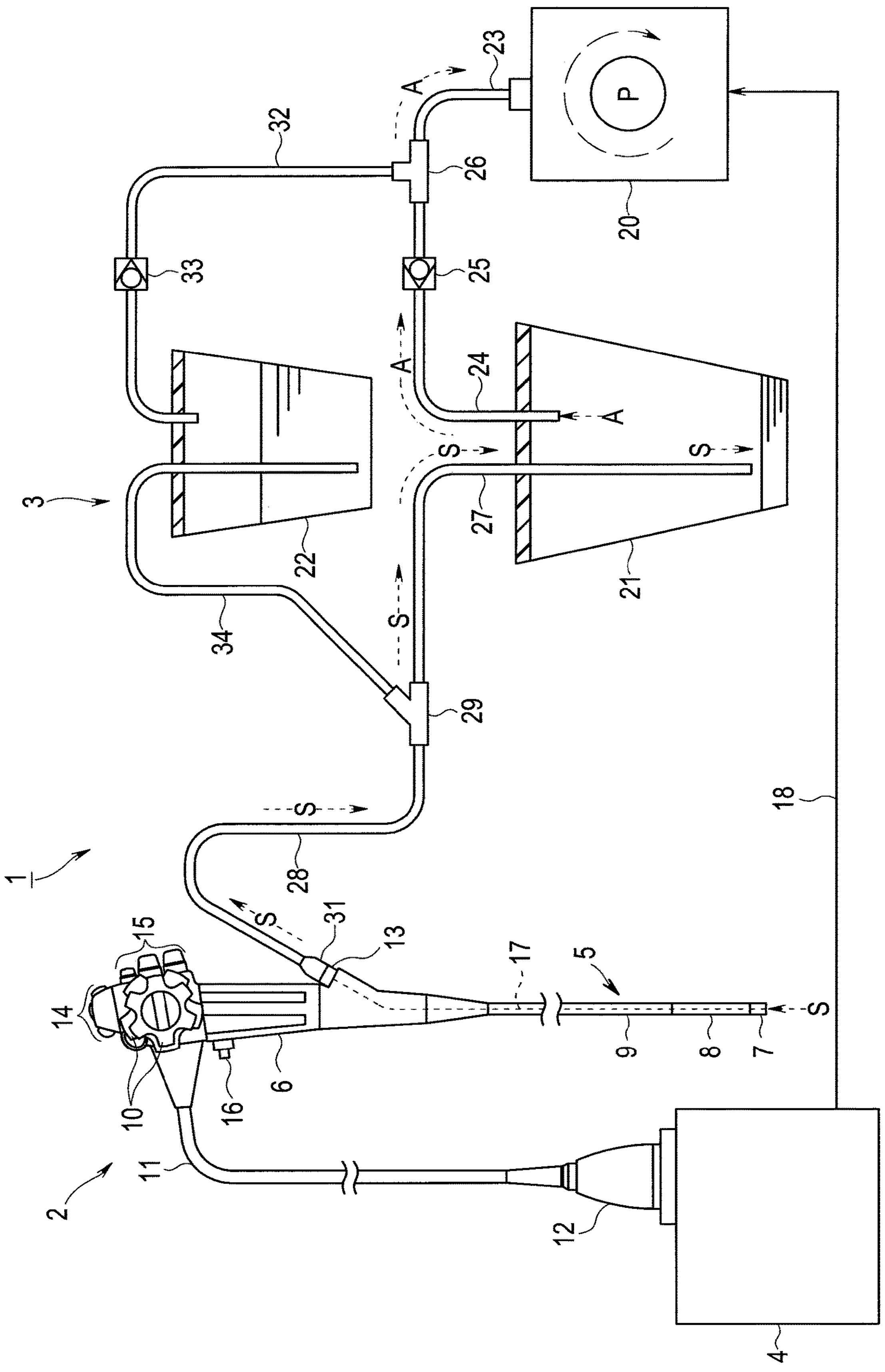
FIG. 3 is a view schematically showing the endoscope system in a suction mode.

On the other hand, when the endoscope system 1 performs a suction operation, the control button 16 is operated in a predetermined manner, and thereby the gas feeding and suction pump unit 20 drives in a predetermined rotation (reverse rotation) direction that is an opposite direction to the direction during gas feeding, as shown in FIG. 3.

The air A suctioned by the gas feeding and suction pump unit 20 is suctioned through the pump tube 23, the T-tube 26, and the gas suction tube 24. Therefore, negative pressure is generated in the liquid draining tank 21.

At this time, the valve in the check valve 25 provided in the gas suction tube 24 opens by the air A that is suctioned, and pressure in the liquid draining tank 21 reduces. Note that in the check valve 33 provided in the gas feeding tube 32, the internal valve is closed by the back pressure of feeding of the air A that is generated in the gas feeding tube 32. Therefore, gas (air) in the liquid feeding tank 22 is blocked by the check valve 33 and is not suctioned by the gas feeding and suction pump unit 20.

In the liquid draining tank 21, the air A inside is drawn into the gas suction tube 24, and negative pressure is generated. Therefore, an inside of the liquid draining tube 27 is suctioned. In this way, an inside of the treatment instrument insertion channel 17 of the endoscope 2 is also suctioned, through the liquid draining tube 27, the Y-tube 29, and the fluid feeding and suction tube 28.

Thereby, in the endoscope system 1, a suction mode for suction the foreign matter S (including gas) such as a liquid and solid substances in the body into the treatment instrument insertion channel 17 from the distal end portion 7 of the insertion portion 5 by bringing the suction conduit system under negative pressure is executed. Note that the foreign matter S that is suctioned into the treatment instrument insertion channel 17 is fed into and stored in the liquid draining tank 21 through the respective tubes 27, 28, and 29.

Note that in the fluid feeding and suction apparatus 3, the component that becomes a contaminated area after end of the procedure by the endoscope 2, for example, the suction conduit system, that is, the liquid draining tube 27, the Y-tube 29, and the fluid feeding and suction tube 28 including the treatment instrument insertion opening connector 31 is discarded. The liquid draining tank 21 may be cleaned and reused or may be discarded after use.

The fluid feeding and suction apparatus 3 may be configured such that all the gas feeding conduit system and the suction conduit system except for the gas feeding and suction pump unit 20 are discarded after use.

From the above explanation, when the foreign matter S such as undigested food and coagulated blood in a body, for example, in a stomach is clogged in the treatment instrument insertion channel 17 of the insertion portion 5 of the endoscope 2 during execution of the suction mode, in the endoscope system 1, it is possible to eliminate the clogging in the treatment instrument insertion channel 17 by easily switching to the liquid feeding mode.

In the endoscope system 1, it is possible to easily perform suction of the foreign matter S including insoluble matter that is residue in a body, for example, in a stomach by switching to the suction mode again. Accordingly, in the endoscope system 1, it is possible to quickly advance a procedure such as identification of a bleeding site by the endoscope 2.

From the above, with the fluid feeding and suction apparatus 3 of the endoscope 2, the endoscope system 1, and the method of suctioning residue by the endoscope of the present embodiment, it is possible to easily switch the suction operation and the liquid feeding operation by a hand-side operation, and quickly perform identification of a bleeding site in a body, for example, in a stomach, by suctioning the insoluble matter that is residue in a body, the foreign matter S and the like. The method for suctioning with the fluid feeding and suction apparatus 3 comprises connecting the endoscopic connection end 31 of the common conduit 28 of the fluid feeding and suction apparatus 3 to the opening 13 of the endoscope 2, and operating the pump 20 of the fluid feeding and suction apparatus 3 in a first mode. In the first mode, operating the pump 20 results in a negative pressure in the fluid suction container 21 of the fluid feeding and suction apparatus 3. In the first mode, a fluid is suctioned through the common conduit 28 from the endoscopic connection end 31 to the second end. The fluid is one or more of undigested food, coagulated blood and physiological saline fed in the subject. In the first mode, the fluid is suctioned from the second end and the fluid suction conduit 27 to the fluid suction container 21. In a second mode, operating the pump 20 results in a positive pressure in the fluid feeding container 22 of the fluid feeding and suction apparatus 3. In the second mode, a fluid from the fluid feeding container 22 flows through the common conduit 28 from the second end to the endoscopic connection end 31. In the second mode, a fluid flows from the fluid feeding container 22 through the fluid feeding conduit 34 and the common conduit 28.

The fluid feeding and suction apparatus 3 of the endoscope system 1 has a simple structure and can be configured at low cost because a device can be used without switching between the liquid feeding conduit system and the suction conduit system by providing the two check valves 25 and 35 in the conduits.

(Modification)

(First Modification)

Figure 4:
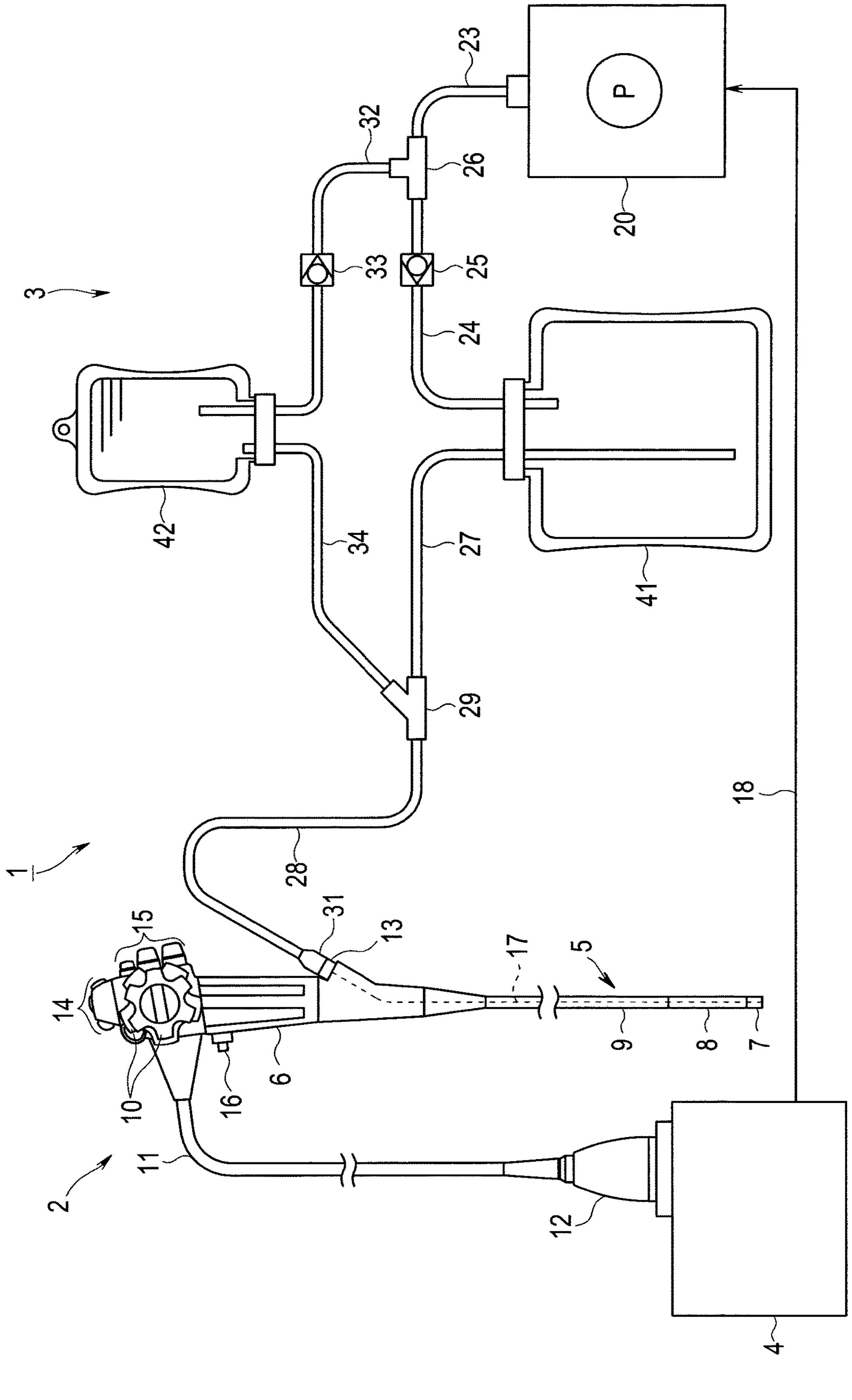
FIG. 4 is a view schematically showing an endoscope system in which a liquid draining pack and a liquid feeding pack of a first modification are provided.

As shown in FIG. 4, in a fluid feeding and suction apparatus 3 of an endoscope system 1, the liquid draining tank 21 may be changed to a liquid draining pack 41, and the liquid feeding tank 22 may be changed to a liquid feeding pack 42.

The liquid draining pack 41 and the liquid feeding pack 42 are polyethylene containers, plastic bottles, or the like. Note that the liquid draining pack 41 is a disposable empty container, and the liquid feeding pack 42 is a pack containing physiological saline, for example.

The fluid feeding and suction apparatus 3 is configured to be simpler, inexpensive, and suitable for single use, by using the liquid draining pack 41 and the liquid feeding pack 42 such as polyethylene containers, or plastic bottles as above. The check valve 25 is provided in the gas suction conduit 24, the check valve 25 configured to allow the suction gas to flow from the fluid suction container 41 to the pump 20, and is configured to prevent the suction gas from flowing from the pump 20 to the fluid suction container 41. The check valve 33 is provided in the gas feeding conduit 32, the check valve 33 is configured to allow the supply gas to flow from the pump 20 to the fluid feeding container 42 and is configured to prevent the supply gas from flowing from the fluid feeding container 42 to the pump 20. The fluid feeding container 42 is configured to contain physiological saline, and the fluid suction container 41 is configured to contain fluid such as undigested food, coagulated blood in a subject and the physiological saline fed. The fluid feeding container 42 includes a first interior space, and a first end of the gas feeding conduit 32 is located in the first interior space. The fluid suction container 41 includes a second interior space, and a first end of the gas suction conduit 24 is located in the second interior space.

(Second Modification)

Figure 5:
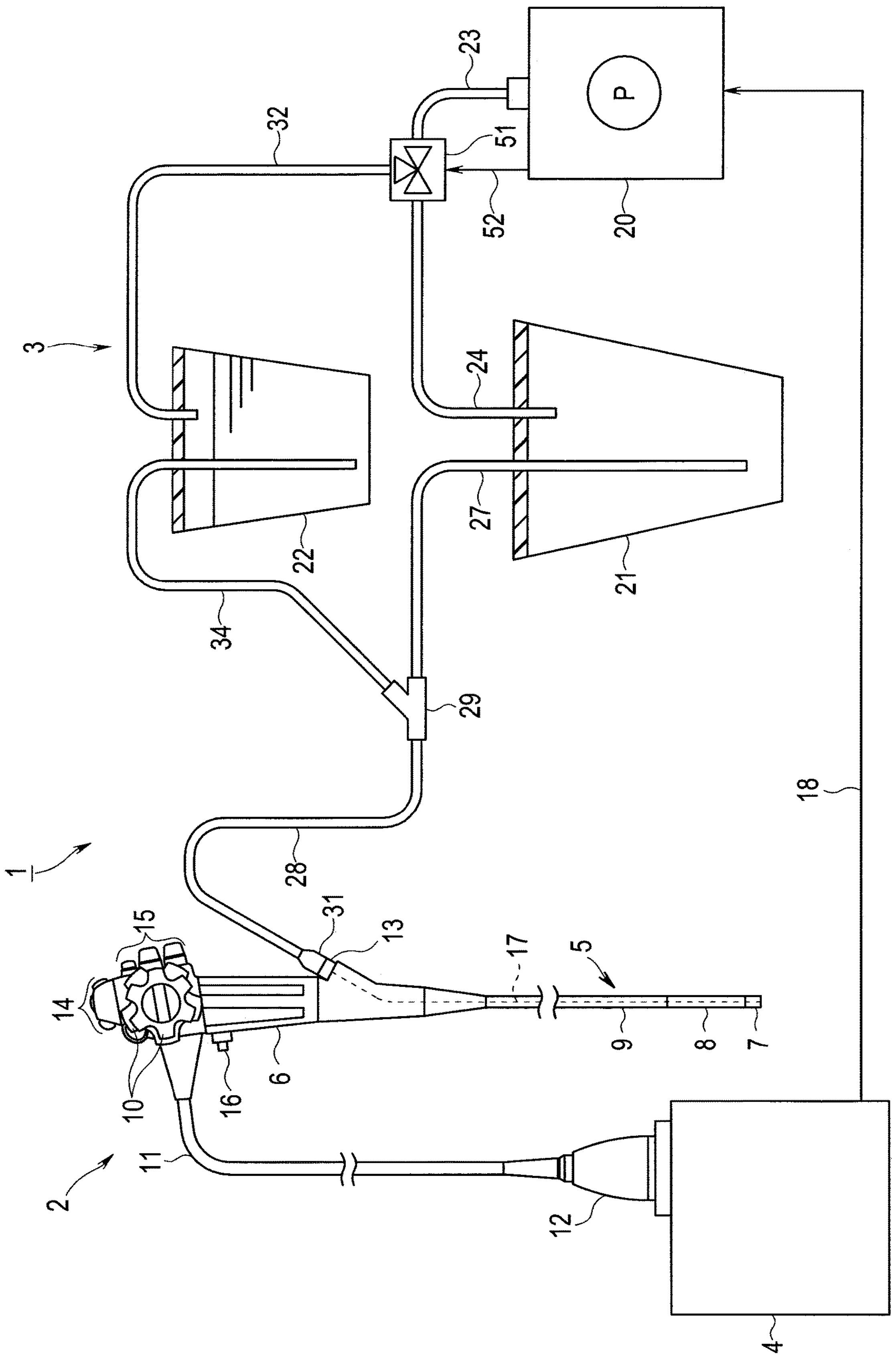
FIG. 5 is a view schematically showing an endoscope system in which a three-way solenoid valve of a second modification is provided.

As shown in FIG. 5, in a fluid feeding and suction apparatus 3 of an endoscope system 1, the T-tube 26 may be changed to a three-way solenoid valve 51 without using the check valves 25 and 33.

The three-way solenoid valve 52 is connected to a pump tube 23, a gas suction tube 24, and a gas feeding tube 32. The three-way solenoid valve 51 is connected to a gas feeding and suction pump unit 20 by a control cable 51.

The gas feeding and suction pump unit 20 switches the three-way solenoid valve 51 according to a rotation direction of an internal pump. Note that the gas feeding and suction pump unit 20 switches the three-way solenoid valve 51 so that the three-way solenoid valve 51 communicates with the gas suction tube 24 during a suction mode (second operational state). On the other hand, the gas feeding and suction pump unit 20 switches the three-way solenoid valve 51 so that the three-way solenoid valve 51 communicates with the gas feeding tube 32 during a liquid feeding mode (first operational state). In the first operational state of the three-way solenoid valve 51, the three-way solenoid valve 51 is configured to allow the supply gas to flow from the pump 20 to the fluid feeding container 22, and is configured to prevent the supply gas to flow from the pump 20 to the fluid suction container 22. In the second operational state of the three-way solenoid valve 51, the three-way solenoid valve 51 is configured to allow the suction gas to flow from the fluid suction container 21 to the pump 20 and to prevent the suction gas from flowing from the fluid feeding container 22 to the pump 20.

Figure 6:
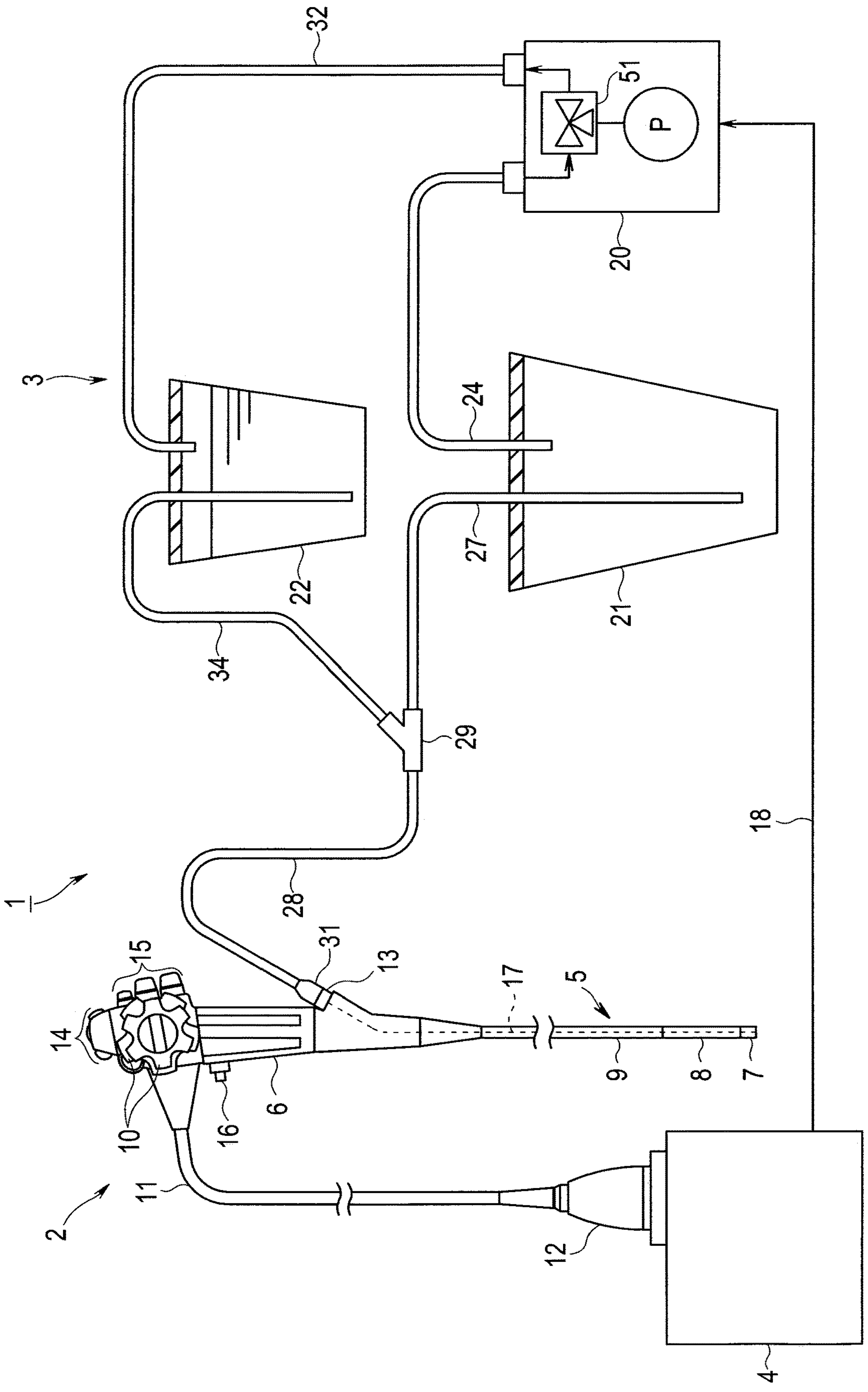
FIG. 6 is a view schematically showing an endoscope system in which the three-way solenoid valve of the second modification is provided in a pump unit.

Note that as shown in FIG. 6, the three-way solenoid valve 51 may be contained in the gas feeding and suction pump unit 20. In this case, the pump tube 23 may be not included, and a configuration is such that the gas suction tube 24 and the gas feeding tube 32 are connected to the gas feeding and suction pump unit 20.

In the endoscope system 1 described above, liquid feeding and suction are enabled by one apparatus. Therefore, when the foreign matter S is clogged in the treatment instrument insertion channel 17 in the endoscope system 1, during the suction mode for quickly removing the foreign matter S including insoluble matter that is residue in a body, for example, in a stomach, it is possible to easily eliminate clogging of the foreign matter S by switching to the liquid feeding mode.

As a result, in the endoscope system 1, it is possible to identify a bleeding site in a body, for example, in a stomach by the endoscope 2 than in the conventional art.

Furthermore, in the fluid feeding and suction apparatus 3, the pump unit 20 having a strong suction force can be used instead of the suction function included by the endoscope 2 in advance. Therefore, the endoscope system 1 can quickly suction the foreign matter S.

Suction of the foreign matter S may be performed by the treatment instrument insertion channel 17 as alternative of a channel that is externally. Therefore, it is possible to reduce a diameter of the insertion portion 5 of the endoscope 2, and it is possible to advance a quick procedure without time and effort to attach a syringe or the like for feeding a liquid during the procedure.

The conduit system of the fluid feeding and suction apparatus 3 is configured to be simple and inexpensive by using a silicon tube or the like that has tube shape. The conduit system of the fluid feeding and suction apparatus 3 becomes a suitable system for single use for the purpose of preventing infection after end of the procedure of the endoscope 2.

Note that the foreign matter S such as food residue and blood in a body, for example, in a stomach does not have to be completely suctioned and removed by the endoscope system 1, but can be suctioned in a range in which identification and treatment of a bleeding site by the endoscope image can be performed.

The present disclosure is not limited to the aforementioned embodiment, but can be properly changed within the range without departing from the gist or the idea of the disclosure that is read from the claims, the entire description, and the drawings.

Example 1. A liquid feeding and draining apparatus, comprising:

- a liquid feeding and draining conduit connected to a treatment instrument insertion opening of an endoscope;
- a liquid feeding conduit and a liquid draining conduit communicating with the liquid feeding and draining conduit and branching;
- a liquid feeding tank connected to the liquid feeding conduit;
- a liquid draining tank connected to the liquid draining conduit;
- a gas feeding conduit connected to the liquid feeding tank;
- a gas suction conduit connected to the liquid draining tank; and
- a pump to which the gas feeding conduit and the gas suction conduit are connected, and configured to feed gas to the gas feeding conduit and provide suction to the gas suction conduit.

Example 2. The liquid feeding and draining apparatus according to Example 1, comprising:

- a first check valve provided in a middle of the gas feeding conduit, with which gas flows from the pump to the liquid feeding tank, and gas does not flow from the liquid feeding tank to the pump; and
- a second check valve provided in a middle of the gas suction conduit, with which gas flows from the liquid draining tank to the pump, and gas does not flow from the pump to the liquid draining tank.

Example 3. The liquid feeding and draining apparatus according to Example 1, comprising:

- a control apparatus connected to the pump and configured to control a rotation direction of the pump; and
- a control switch connected to the control apparatus and configured to switch the rotation direction of the pump.

Example 4. The liquid feeding and draining apparatus according to Example 3,

- wherein the control switch is placed at an operation portion of the endoscope.

Example 5. The liquid feeding and draining apparatus according to Example 1,

- wherein the liquid feeding tank is a container containing physiological saline, and
- the liquid draining tank is an empty container.

Example 6. The liquid feeding and draining apparatus according to Example 5,

- wherein the liquid feeding tank and the liquid draining tank are disposable polyethylene packs or plastic containers.

Example 7. An endoscope system, comprising:

- an endoscope including a treatment instrument insertion opening, and a channel communicating with the treatment instrument insertion opening; and
- a liquid feeding and draining apparatus connected to the endoscope, wherein the liquid feeding and draining apparatus comprises
- a liquid feeding and draining conduit connected to the treatment instrument insertion opening,
- a liquid feeding conduit and a liquid draining conduit communicating with the liquid feeding and draining conduit and branching,
- a liquid feeding tank connected to the liquid feeding conduit,
- a liquid draining tank connected to the liquid draining conduit,
- a gas feeding conduit connected to the liquid feeding tank,
- a gas suction conduit connected to the liquid draining tank, and
- a pump to which the gas feeding conduit and the gas suction conduit are connected, and configured to feed gas to the gas feeding conduit and provide suction to the gas suction conduit.

Example 8. The endoscope system according to Example 7, comprising:
- a control apparatus connected to the pump and configured to control a rotation direction of the pump; and
- a control switch connected to the control apparatus and configured to switch the rotation direction of the pump.

Example 9. The endoscope system according to Example 7, wherein the liquid feeding tank is a container containing physiological saline, and the liquid draining tank is an empty container.

Example 10. The endoscope system according to Example 9, wherein the liquid feeding tank and the liquid draining tank are disposable polyethylene packs or plastic containers.

Example 11. A method for suctioning residue by an endoscope system, comprising:
- connecting a liquid feeding and draining conduit of a liquid feeding and draining apparatus to a treatment instrument insertion opening of an endoscope;
- driving a pump of the liquid feeding and draining apparatus in a predetermined rotation direction;
- bringing an inside of a liquid draining tank of the liquid feeding and draining apparatus under negative pressure; and
- suctioning foreign matter that is residue in a subject into the liquid draining tank through a channel communicating with the treatment instrument insertion opening and provided in an insertion portion of the endoscope.

Example 12. The method for suctioning residue by an endoscope system according to Example 11, comprising:

when the foreign matter is clogged in the channel,
- driving the pump of the liquid feeding and draining apparatus in an opposite rotation direction to suction of the pump of the liquid feeding and draining apparatus;
- bringing an inside of the liquid feeding tank of the liquid feeding and draining apparatus under positive pressure;
- feeding a liquid stored in the liquid feeding tank to the channel; and
- discharging the foreign matter into the subject through the channel.

What is claimed is:

1. A fluid feeding and suction apparatus, comprising:
- a common conduit including an endoscopic connection end and a second end, the second end connected to a branch conduit;
- a fluid feeding conduit in fluid communication with the common conduit via the branch conduit;
- a fluid suction conduit in fluid communication with the common conduit via the branch conduit;
- a fluid feeding container configured to be connected to the fluid feeding conduit;
- a fluid suction container configured to be connected to the fluid suction conduit;
- a gas feeding conduit connected to the fluid feeding container, through which a supply gas is supplied;
- a gas suction conduit connected to the fluid suction container, through which a suction gas is drawn;
- a single pump connected to the gas feeding conduit and the gas suction conduit, the single pump being switchable between a gas feeding operation and a gas suction operation;
- a first check valve provided in the gas suction conduit, the first check valve being closed when the single pump performs the gas feeding operation and being opened when the single pump performs the gas suction operation; and
- a second check valve provided in the gas feeding conduit, the second check valve being opened when the single pump performs the gas feeding operation and being closed when the single pump performs the gas suction operation.

2. The fluid feeding and suction apparatus according to claim 1, further comprising:
- a first check valve provided in the gas feeding conduit, the first check valve configured to:
  - allow the supply gas to flow from a pump to the fluid feeding container, and
  - prevent the supply gas from flowing from the fluid feeding container to the pump; and
- a second check valve provided in the gas suction conduit, the second check valve configured to:
  - allow the suction gas to flow from the fluid suction container to the pump, and
  - prevent the suction gas from flowing from the pump to the fluid suction container.

3. The fluid feeding and suction apparatus according to claim 1, further comprising:
- a three-way solenoid valve,
- wherein, in a first operational state of the three-way solenoid valve, the three-way solenoid valve is configured to allow the supply gas to flow from a pump to the fluid feeding container, and configured to prevent the supply gas from flowing from the pump to the fluid suction container, and
- wherein, in a second operational state of the three-way solenoid valve, the three-way solenoid valve is configured to allow the suction gas to flow from the fluid suction container to the pump and to prevent the suction gas from flowing from the fluid feeding container to the pump.

4. The fluid feeding and suction apparatus according to claim 1, further comprising:
- a controller configured to switch rotation direction of a pump.

5. The fluid feeding and suction apparatus according to claim 1, wherein the fluid feeding container is configured to contain physiological saline, and wherein the fluid suction container is configured to contain fluid.

6. The fluid feeding and suction apparatus according to claim 1, wherein the fluid feeding container and the fluid suction container are formed from polyethylene or plastic.

7. The fluid feeding and suction apparatus according to claim 1, wherein the fluid feeding container includes a first interior space, and wherein a first end of the gas feeding conduit is located in the first interior space.

8. The fluid feeding and suction apparatus according to claim 7, wherein the fluid suction container includes a second interior space, and wherein a first end of the gas suction conduit is located in the second interior space.

9. An endoscope system, comprising:

the fluid feeding and suction apparatus according to claim 1;

an endoscope; and a pump connected to the gas feeding conduit and the gas suction conduit, the pump configured to feed the supply gas to the gas feeding conduit and to suction the suction gas from the gas suction conduit, wherein the endoscope includes a first opening, a distal end opening, and a channel connecting the first opening and the distal end opening, and wherein the endoscopic connection end of the fluid feeding and suction apparatus is connected to the first opening of the endoscope.

10. The endoscope system according to claim 9, further comprising:

a controller configured to switch a rotation direction of the pump.

11. The endoscope system according to claim 9, wherein the endoscope includes an operation portion including:

a controller configured to switch a rotation direction of the pump, and a control switch configured to transmit a signal to the controller.

12. The fluid feeding and suction apparatus according to claim 1, further comprising:

a pump connected to the gas feeding conduit and the gas suction conduit, the pump configured to feed the supply gas to the gas feeding conduit and to suction the suction gas from the gas suction conduit.

13. The fluid feeding and suction apparatus according to claim 1, wherein the fluid feeding and suction apparatus is configured to be switched between a first operational state and a second operational state, wherein, in the first operational state, the common conduit is configured to:

fluidly communicate with the fluid feeding conduit; and feed a fluid to the endoscopic connection end, and wherein, in the second operational state, the common conduit is configured to:

fluidly communicate with the fluid feeding conduit; and suction a fluid from the endoscopic connection end.

14. The fluid feeding and suction apparatus according to claim 13, further comprising:

a controller configured to switch between the first operational state and the second operational state.

15. The fluid feeding and suction apparatus according to claim 14, wherein the controller is configured to:

receive a signal; and cause a pump to switch between the first operational state and the second operational state based on the signal.

16. The fluid feeding and suction apparatus according to claim 13, wherein in the first operational state, the branch conduit is configured to:

allow a fluid to flow from the fluid feeding conduit to common conduit; and prevent the fluid from flowing from the common conduit to the fluid suction conduit.

17. The fluid feeding and suction apparatus according to claim 1, wherein the endoscopic connection end is configured to airtightly connect to a treatment instrument insertion channel of an endoscope.

18. The fluid feeding and suction apparatus according to claim 1, further comprising:

a first check valve provided in the gas suction conduit, the first check valve configured to:

be opened by the suction gas drawn through the gas suction conduit, and be closed by the supply gas supplied through the gas feeding conduit.

19. The fluid feeding and suction apparatus according to claim 1, further comprising:

a second check valve provided in the gas suction conduit, the second check valve configured to:

be opened by the supply gas supplied through the gas feeding conduit, and be closed by the suction gas drawn through the gas suction conduit.

20. The fluid feeding and suction apparatus according to claim 1, wherein an end of the fluid suction conduit is provided closer to a bottom of the fluid suction container than an end of the gas suction conduit.

* * * * *